United States Patent [19]
Cohen et al.

[11] Patent Number: 5,643,717
[45] Date of Patent: *Jul. 1, 1997

[54] SUBSTRATE USEFUL FOR SEPARATING MODIFIED OLIGONUCLEOTIDES

[75] Inventors: Aharon S. Cohen, Brookline; Maria Vilenchik, Natick, both of Mass.

[73] Assignee: Hybridon, Inc., Worcester, Mass.

[*] Notice: The portion of the term of this patent subsequent to Dec. 16, 2012, has been disclaimed.

[21] Appl. No.: 32,856

[22] Filed: Mar. 16, 1993

Related U.S. Application Data

[63] Continuation-in-part of Ser. No. 991,466, Dec. 16, 1992, Pat. No. 5,420,265.

[51] Int. Cl.$^6$ ............................................. C12Q 1/68
[52] U.S. Cl. ................................... 435/6; 525/329.4
[58] Field of Search ....................... 204/182.8; 526/93, 526/173; 525/329.4; 435/6

[56] References Cited

U.S. PATENT DOCUMENTS

| | | | |
|---|---|---|---|
| 4,816,571 | 3/1989 | Andrus et al. | 536/25.3 |
| 4,865,706 | 9/1989 | Karger et al. | 204/182.8 |
| 4,865,707 | 9/1989 | Karger et al. | 204/182.8 |
| 4,965,349 | 10/1990 | Woo et al. | 536/25.3 |
| 5,003,059 | 3/1991 | Brennan | 536/27 |
| 5,047,524 | 9/1991 | Andrus et al. | 536/25.31 |
| 5,098,539 | 3/1992 | Shieh | 204/182.8 |
| 5,112,460 | 5/1992 | Karger et al. | 204/182.8 |
| 5,262,530 | 11/1993 | Andrus et al. | 536/25.31 |

FOREIGN PATENT DOCUMENTS

| | | |
|---|---|---|
| 0339780 | 11/1989 | European Pat. Off. . |
| 0497448 | 8/1992 | European Pat. Off. . |

OTHER PUBLICATIONS

Sambrook et al., "Molecular Cloning," Denaturing Poly-acryl–amide gels, pp. 13.45–13.55., 1989.
Grierson, in Gel Electrophoresis of Nucleic Acids, Ed. by Rickwood pp. 15–19, 1990.
Hejrten (1967) *Chromatographic Rev.* 9:122–213.
Burgers et al. (1979) *Biochemsitry* 18:592–596.
Edge et al. (1981) *Nature* 292:756–762.
Murakami et al. (1985) *Biochemistry* 24:4041–4046.
Stec et al. (1985) *J. Chromatogr.* 326:263–280.
Froehler (1986) *Tetrahedron Lett.* 27:5575–5578.
Garegg et al. (1986) *Tetrahedron Lett.* 27:4051.
Agrawal et al. (1987) *Tetrahedron Lett.* 28:3539–3542.
Agrawal et al. (1988) *Proc. Natl. Acad. Sci. (USA)* 85:7079–7083.
Cohen et al. (1988) *Proc. Natl. Acad. Sci. (USA)* 85:9660–9663.
Current Protocols In Molecular Biology, Green Publishing and Wiley Interscience, N.Y. 1988.
Sarin et al. (1988) *Proc. Natl. Acad. Sci. (USA)* 85:7448–7451.
Agrawal et al. (1989) *Proc. Natl. Acad Sci. (USA)* 86:77790–7794.
Agrawal et al. (1989) *Nucleosides and Nucleotides* 8(5&6):819–823.
Wu et al. (1989) *J. Chromatogr.* 480:141–155.
Agrawal et al. (1990) *Nucleic Acids Res.* 18:5419–5423.
Agrawal et al. (1990) *J. Chromatogr.* 509:396–399.
Ansorge et al. (1990) *Nucleic Acids Res.* 18:3419–3420.
Bigelow et al. (1990) *J. Chromatogr.* 533:133–140.
Cohen et al. (1990) *J. Chromatogr.* 516:49–60.
Heiger et al. (1990) *J. Chromatogr.* 516:33–48.
Swerdlow et al. (1990) *J. Chromatogr.* 516:61–67.

(List continued on next page.)

*Primary Examiner*—Scott W. Houtteman
*Attorney, Agent, or Firm*—Hale and Dorr

[57] ABSTRACT

Disclosed is a substrate useful for separating unmodified and modified mononucleotides and oligonucleotides. The substrate includes at least 12% polymer in at least 50% (volume:volume) organic solvent, the organic solvent being a denaturing agent. This substrate is easily removable from the capillary using low pressure. Also provided is a method of separating unmodified and modified mononucleotides and oligonucleotides utilizing this substrate.

11 Claims, 4 Drawing Sheets

OTHER PUBLICATIONS

Brumley et al. (1991) *Nucleic Acids Res.* 19:4121–4126.
Chen et al. (1991) *J. Chromatogr.* 559:237–246.
Guttman et al. (1991) *Anal. Chem.* 63:2038–2042.
Swerdlow et al. (1991) *Anal. Chem.* 63:2835–2841.
Zhang et al. (1991) *Clin. Chem.* 37:1492–1496.
Agrawal et al. (1992) *TIBTECH* 10:152–158.
Bergot et al. (1992) *J. Chromatogr.* 559:35–47.
Metelev et al. (1992) *Analyt. Biochem.* 200:342–346.
Rocheleau et al. (1992) *Electrophoresis* 13:484–486.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

CGTATAGCCT GATGTCATAG CCGAT 25

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:2:

GACTCGAGGT CTGCTAACCT AGAT 24

SUBSTRATE USEFUL FOR SEPARATING MODIFIED OLIGONUCLEOTIDES

CROSS-REFERENCE TO RELATED APPLICATION

This patent application is a continuation-in-part of patent application Ser. No. 07/991,466, filed Dec. 16, 1992, entitled ANALYTICAL TECHNIQUE FOR OLIGONUCLEOTIDE ANALOGS now U.S. Pat. No. 5,420,265, issued May 30, 1995.

FIELD OF THE INVENTION

This invention relates to the separation of mononucleotides and oligonucleotides. More particularly, this invention relates to the separation and characterization of modified and unmodified mononucleotides and oligonucleotides by high performance capillary electrophoresis.

BACKGROUND OF THE INVENTION

Oligonucleotides that are complementary or "antisense" to specific genes or RNA sequences are relatively small, synthetic molecules having an average molecular weight of about 10 kilodaltons (kD). These antisense molecules have had widespread use in the field of selective gene regulation with consequent therapeutic implications. Phosphate backbone modification of such oligonucleotides provides nuclease resistance and greatly enhances the usefulness of these analogs. Such modifications include the substitution of phosphodiester internucleotide linkages with linkages such as methylphosphonates (Murakami et al. (1986) *Biochem.* 24:4041–4046; Agrawal et al. (1987) *Tetrahedron Lett.* 28:3539–3542; Sarin et al. (1988) *Proc. Nat. Acad. Sci. (USA)* 85:7448–7451), phosphorothioates (Burgers et al. *Biochemistry* 18:592–596; Agrawal et al. (1988) *Proc. Natl. Acad. Sci. (USA)* 85:7079–7083; Agrawal et al. (1989) *Nucleosides and Nucleotides* 8:819–823; Agrawal et al. (1989) *Proc. Natl. Acad. Sci. (USA)* 86:7790–7794), and phosphoramidates (Agrawal et al. (1988) *Proc. Natl. Acad. Sci. (USA)* 85:7079–7083; Agrawal et al. (1989) *Nucleosides and Nucleotides* 8:819–823).

Of special interest are phosphorothioate analogs in which one non-bridging oxygen atom has been substituted for a sulfur atom on the phosphate group in each internucleotide phosphate linkage. This modification is a conservative substitution which increases nuclease resistance without significantly impairing the hybridization of the antisense molecule with target mRNA. As synthesized, these modified oligonucleotides or analogs are usually found as diastereomeric mixtures due to chirality at their phosphorous group. In a context of new drug research, development and manufacturing of such analogs requires that the issues of oligomer length, base composition, base sequence, chemical purity, and stereochemical purity be successfully addressed.

Synthetic oligonucleotides are presently used in most laboratories using molecular biology techniques. As synthesized, these oligonucleotides generally exist as mixtures of truncated oligonucleotides in addition to the desired oligonucleotide. Since the purity and chemical identity of a particular oligonucleotide is crucial to many applications, the ability to characterize and separate synthetic oligonucleotides analogs on a routine basis is important.

The absolute length and the degree of length heterogeneity of prepared oligonucleotides have been assessed by electrophoresis in high resolution denaturing polyacrylamide slab gels (PAGE) (see e.g., *Current Protocol in Molecular Biology*, Green Publishing and Wiley Interscience, New York, 1988) and by capillary gel electrophoresis through cross-linked polyacrylamide (6% T, 5% C) gels (Hjerten (1967) *Chromatogr. Rev.* 9:122–213) containing from 10% to less than 30% (vol.:vol.) formamide (Rocheleau et al. (1992) *Electrophoresis* 13:484–486). Detection of oligonucleotides separated on such gels has been accomplished by autoradiography and laser-induced fluorescence. These methods have not proven suitable for separating modified oligonucleotides. Furthermore, some of these gels, once used, are not easily removable from the capillary. To remedy this problem, gels containing up to 5% acrylamide monomer have been polymerized before filling the capillary (EPO 497 480). Ultrathin slab gels (less than 100 µm in thickness) have also been used for high speed DNA sequencing (Brumley et al. (1991) *Nucleic Acids Res.* 19:4121–4126; Ansorge et al. (1990) *Nucleic Acids Res.* 18:3419–5420). Alternative separation methods include ion exchange chromatography, reversed phase high pressure liquid chromatography (HPLC), and gel high performance capillary electrophoresis (HPLC) (see e.g., Edge et al. (1981) *Nature* 292:756–762; U.S. Pat. No. 4,865,707).

Oligonucleotides with phosphorothioate linkages are more difficult to resolve than phosphodiester-linked DNA due to the existence of diastereomer isomers ($2^n$, where n=the number of chiral centers, which is equivalent to the number of phosphate groups). In addition, difficulty in resolution may be due to increased hydrophobicity of the former. These molecules, when separated, interact hydrophobically with ion exchange column supports and in many cases co-elute. Thus, they cannot be separated by the above methods in their existing formats.

The separation of phosphorothioate oligonucleotide analogs is problematic for other reasons as well. When phosphorothioate oligonucleotides are assembled using either methoxyphosphoramidite or H-phosphate chemistry, they are in the form of diastereomeric mixtures due to chirality at their phosphorous groups. As a result, although they migrate through polyacrylamide gels and HPLC columns like their corresponding phosphodiester counterparts, phosphorothioate oligonucleotides give broader peaks and run more slowly than phosphodiesters because of their increased hydrophobicity. They are also known to interact with the HPLC column support. In addition, phosphorothioates run into stereochemical problems when separated by reversed phase HPLC. General analytical methods have not been devised for establishing the ratio of the optical isomers at each unsymmetrical substitution phosphorous linkage in an analog having many such sites of local chirality.

HPLC of oligodeoxyribonucleotides containing one or two phosphorothioate internucleotide linkages using a reversed-phase column (RP-HPLC) has been reported (Stec et al. (1985) *J. Chromatogr.* 326:263–280; Agrawal et al. (1990) *Nucleic Acids Res.* 18:5419–5423). However, this method is of limited use because of the small differences in the hydrophobicity of these analogs with increasing chain length (Agrawal et al. (1990) *J. Chromatogr.* 509:396–399).

Separation of oligodeoxyribonucleotide phosphorothioates containing 10 or fewer nucleotides has also been achieved by HPLC on strong anion-exchange (SAX) columns (Agrawal et al. (1990) *J. Chromatogr.* 509:396–399). In this method, oligonucleotide phosphorothioates were converted to their phosphodiester counterparts in one step, and then were analyzed by HPLC. Unfortunately, oligonucleotides phosphorothioates containing more than 10 nucleotides can not be analyzed by this method because of their strong interaction with the SAX medium. Thus the separation of oligonucleotide phosphorothioates by this method is limited by its oligonucleotide length dependency.

Length-dependent separation of phosphorothioate analogs by HPLC using a weak anion-exchange (WAX) column has also been accomplished (Meletev et al. (1992) *Analyt. Biochem.* 200:342-346). However, the peaks obtained were broader than those obtained for their phosphodiester counterparts, possibly because of their diastereomeric backbone. Ion-pair HPLC has also been used to analyze oligonucleotide phosphorothioates (Bigelow et al. (1990) *J. Chromatogr.* 533:131-140), but length-dependent separation was not achieved.

Thus, what is needed are better analytical methods of separating unmodified and modified mononucleotides and oligonucleotides cleanly, rapidly, efficiently, and which are not limited by the size range or modification of the molecules being analyzed. In addition, methods enabling the quick and easy removal and replacement of the substrate used for separation are also needed.

SUMMARY OF THE INVENTION

A novel substrate and method of its use have been developed for the separation and characterization of unmodified and modified mononucleotides and oligonucleotides differing by as little as a single base. An advantage to this method is the relative ease by which samples of less than 1 nanogram in microliter or smaller volumes can be conveniently handled with on-line UV detection. Another advantage is the relative ease with which the separation substrate can be replaced with new substrate after use. Relative to slab gel and on-line UV regular gel high performance capillary electrophoresis (HPCE) operation, this new formulation can be very useful for in process analysis as well as for purity assessment of antisense nucleotides in the pharmaceutical industry.

As used herein, a "mononucleotide analog" or "modified mononucleotide" is a base, including purines and pyrimidines, or modifications thereof, attached to the 1' end of the deoxyribose or ribose sugar, or modifications thereof, which is attached at its 5' position to a phosphate group. A "5'-substituted mononucleotide analog" includes a deoxyribose or ribose sugar, which is attached at its 5' position to a chemical group other than the phosphate group found in native nucleotides. Preferable chemical groups include alkyl phosphonates, phosphorothioates, alkyl phosphorothioates, phosphoramidates, phosphorodithioates, phosphatediesters, and phosphate triesters.

A "3'-substituted mononucleotide analog" includes a deoxyribose or ribose sugar attached at its 3' position to a chemical group other than the hydrogen found in native nucleotides.

"Modified oligonucleotide" or "oligonucleotide analog", as used herein, is a molecule containing at least two ribonucleotides or deoxyribonucleotides which are covalently linked via at least one synthetic linkage. A "synthetic internucleotide linkage" is a linkage other than a phosphodiester linkage between the 5' end of one nucleotide and the 3' end of another nucleotide in which the 5' internucleotide phosphate has been replaced with any number of chemical groups. Preferable synthetic linkages include alkyl phosphonates, phosphorothioates, alkyl phosphorothioates, phosphoramidates, phosphorodithioates, phosphatediesters and phosphate triesters. A "3',5'-substituted" mononucleotide or oligonucleotide is a modified mononucleotide or oligonucleotide having a sugar which, at both its 3' and 5' positions is attached to a chemical group other than a hydroxyl group (at its 3' position) and other than a phosphate group (at its 5' position). A modified oligonucleotide may also be capped.

Preferable polymers include polyacrylamide, methyl cellulose and derivatives thereof, and polyvinyl alcohol. In one preferred aspect, the substrate of the invention includes at least 12% T polymerized acrylamide (or polyacrylamide) in at least 50% and preferably 60% (volume:volume) organic solvent. The term "T" refers to the percent of monomers (mass:volume). In one aspect of the invention, the substrate is linear polyacrylamide. In some embodiments, the substrate contains about 12% to 20% T polyacrylamide, with from about 13% to 18% T being optimal. A linear gradient of about 13% to 18% T polyacrylamide is present in some aspects of the invention. The acrylamide may be non-crosslinked in some aspects of the invention. In other aspects the acrylamide may contain up to 1% cross-linking.

Useful organic solvents include formamide, urea, and sodium dodecyl sulfate. A preferable organic solvent is formamide present at a concentration of at least 60% (volume:volume). In some embodiments, the invention includes a substrate containing 18% T polyacrylamide in formamide, and may further include urea.

This invention also provides a method of separating unmodified and modified mononucleotides and oligonucleotides using the above-described substrate. The method includes contacting the substrate, which is in a high performance capillary, with the mononucleotide and/or oligonucleotides to be separated. An electric field greater than 200 volts/centimeter is applied across the substrate in the capillary, and the separated mononucleotides and/or oligonucleotides are detected. In preferred embodiments of the invention, an electric field of about 400 volts/cm is applied across the substrate.

In another aspect of the invention the substrate is removed from the capillary after the detection step. Removal is preferably accomplished by applying at least 30 psi pressure on one end of the capillary. Such pressure can be exerted manually or by means of an automated system.

Molecules capable of being separated by this method include unmodified mononucleotides and oligonucleotides and mononucleotide and oligonucleotide analogs having from 1 to 50 bases. This method is also useful for separating such mononucleotides and oligonucleotide analogs having from 1 to 150, and even up to about 300 bases.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1A:
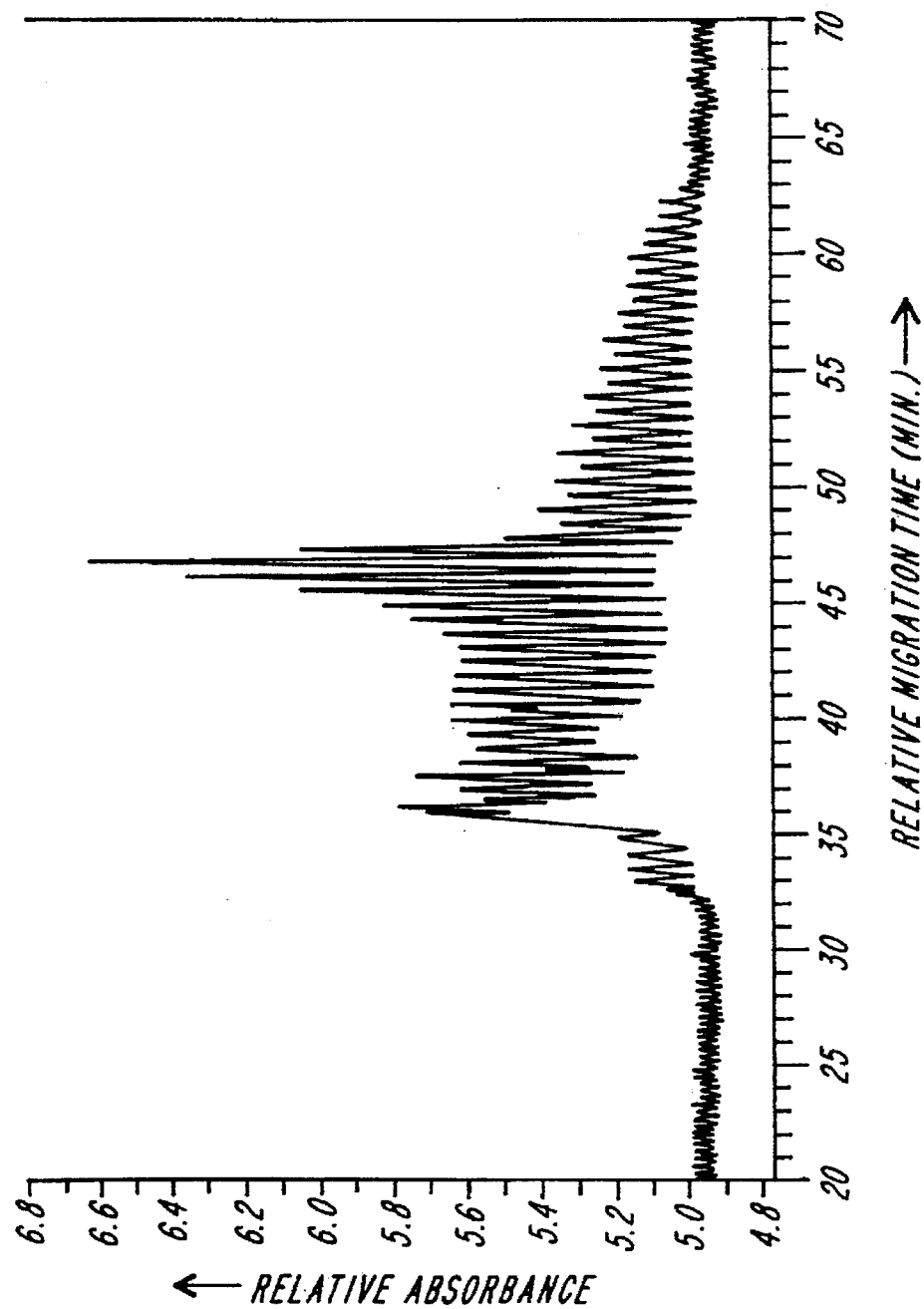
FIG. 1A is an electropherogram demonstrating the electrophoretic separation by high performance capillary electrophoresis of phosphorothioate failure sequences ranging in length from 1 to 50 bases in length.

This invention provides a novel substrate and methods of using that substrate to separate unmodified and modified mononucleotides and oligonucleotides which may differ by only one base.

HPCE utilizing the novel substrate of the invention holds a unique position in the field of oligodeoxynucleotide separation due to its resolution power, ability to determine purity, speed, and automation. Because of the low current generated ($\mu$A) from the narrow bore columns (25 to 200 $\mu$m, inner diameter), high electric fields (hundreds of volts/cm) without excess Joule heating can be employed, resulting in very rapid, high resolution separations. As an instrument technique, HPCE is highly reproducible, is amenable to automation, and is thus a powerful alternative tool for antisense analysis. Furthermore, the substrate is unique because it is easily removable and replaceable.

Traditional capillary electrophoresis suggests the application of electric fields lower than 200 V/cm with low ionic strength buffer (not higher than 0.1M Tris-borate-EDTA (TBE)) and low gel concentration in aqueous media for the separation of oligonucleotides. However, it has been discovered that the use of 0.2M TBE buffer and an electric field of at least 200 V/cm gives very high resolution in certain gel substrates for the separation of oligonucleotide analogs.

The substrate used is a polymer such as polyacrylamide, methyl cellulose, polyvinyl alcohol, or derivatives thereof. The polymer may be up to 1% cross-linked but need not be cross-linked at all. It is important that the concentration of polymer in the capillary be 12% or higher to achieve this kind of resolution and efficiency. No gradient of polymer is required, but linear gradients of, for example, from about 12% to 20%, or more preferably, from about 13% to 18% polymer may be used.

The polymer must be suspended in at least 50% (volume: volume) organic solvent. Useful organic solvents are also denaturing agents which keep the oligonucleotides from assuming secondary structure, an obstacle to clean separation. Such solvents include formamide, urea, and sodium dodecyl sulfate, among others. One particularly useful organic solvent is formamide. To improve denaturation even more, a high concentration of urea (7 to 8.3M) may also be added. In the case of acrylamide, polymerization may be achieved by adding ammonium persulfate and a free radical catalyst such as N,N,N',N'-tetramethylenediamine (TEMED) to the acrylamide solution. The substrate solution is then placed into the capillary where it polymerizes. A useful capillary is a microcapillary column (25 to 200 $\mu$m inner diameter) made of fused silicon, as described in U.S. Pat. Nos. 4,865,706 and 5,112,460.

The molecules which can be successfully separated on this substrate include unmodified mononucleotides and oligonucleotides and modified mononucleotides and oligonucleotides (analogs) such as 3'-, 5'-, and 3', 5'-substituted mononucleotides and oligonucleotides, and mononucleotides and oligonucleotide analogs having at least one phosphate group replaced with a chemical group such as a phosphorothioate, phosphorodithioate, alkyl phosphonate, alkyl phosphorothioate, phosphate ester, phosphate diester, phosphate triester, and phophoramidate, among others. An oligonucleotide analog can have at least one artificial or synthetic (i.e., non-phosphodiester) internucleotide linkage formed by such a chemical group. The preparation of these molecules is well known in the art (reviewed in Agrawal et al. (*Trends in Biotechnol.* (1992) 10:152–158). For example, monomeric and oligomeric phosphorothioate analogs can be prepared using methods well known in the field such as methoxyphosphoramidite (see, e.g., Agrawal et al. (1988) *Proc. Natl. Acad. Sci.* (USA) 85:7079–7083) or H-phosphorate (see, e.g., Froehler (1986) *Tetrahedron Lett.* 27:5575–5578) chemistry. The synthetic methods described in Bergot et al. (*J. Chromatog.* (1992) 559:35–47) can also be used. The products of these syntheses may include failure sequences as well as the desired oligonucleotide sequence. The failure sequences have at least one less base than the desired oligonucleotide, but the position of the missing base is unknown without subsequent sequencing analysis.

In order to separate the failure sequences from the desired oligonucleotides so produced, or in order to distinguish, characterize, and isolate different desired mononucleotides and/or oligonucleotide species from each other, the molecules to be examined are analyzed by HPCE using a capillary electrophoresis apparatus. Such as instrument is well known in the field (see e.g., Cohen et al. (1988) *Proc. Natl. Acad. Sci.* (USA) 85:9660–9663). The molecules to be separated are injected into the capillary by siphoning (in the case of open tube applications). Alternatively, the sample may be electrophoretically injected into the column by dipping the cathodic end of the capillary into the sample solution and applying a field of 400 v/cm for 1 to 3 sec. The sample is then run through the gel, and the separated analogs detected by UV, infrared, fluorescence, laser-induced fluorescence or other external monitoring methods.

Figure 1B:
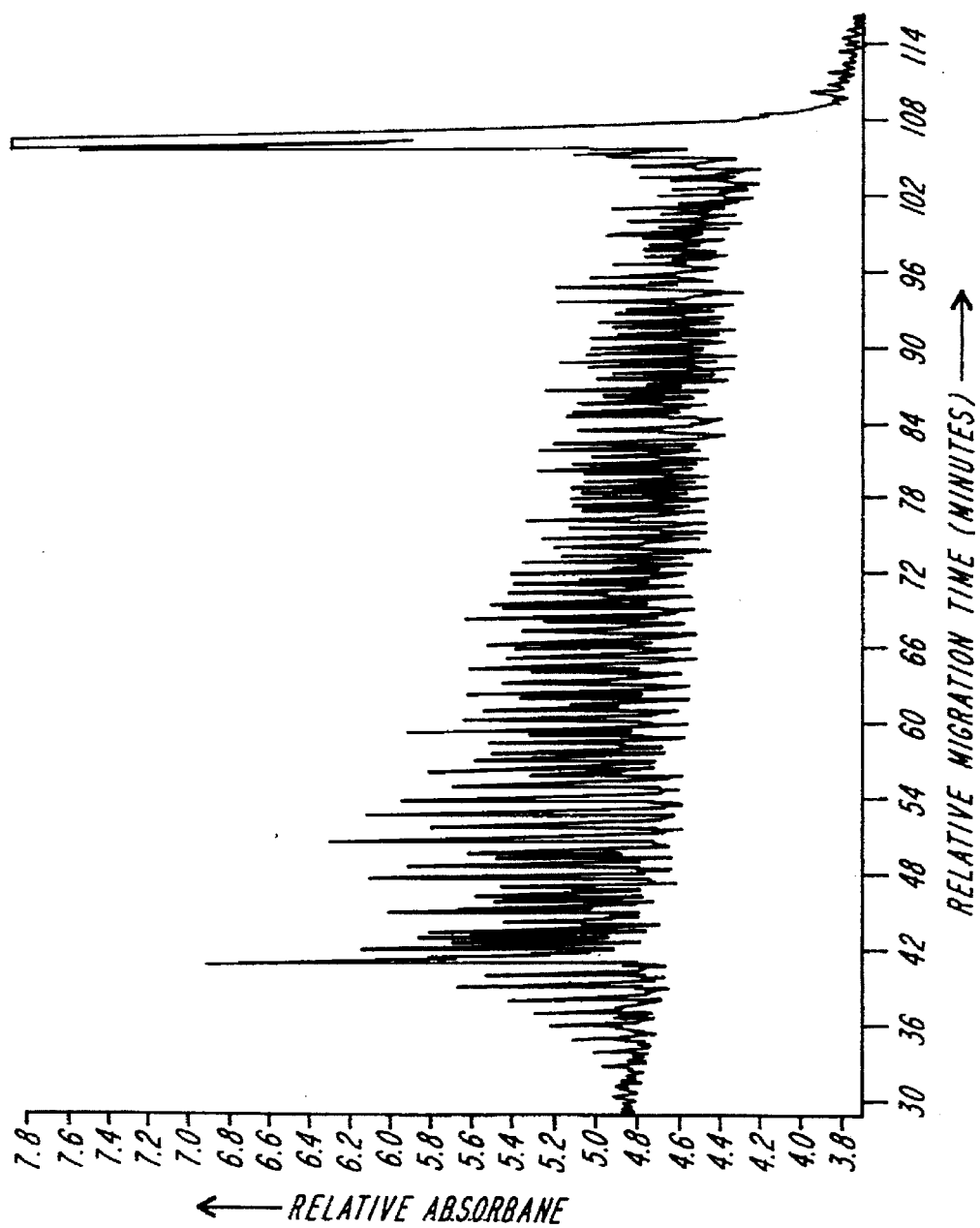
FIG. 1B is an electropherogram demonstrating the electrophoretic separation by high performance capillary electrophoresis of phosphorothioate failure sequences ranging in length from 1 to 75 bases in length.
Figure 3:
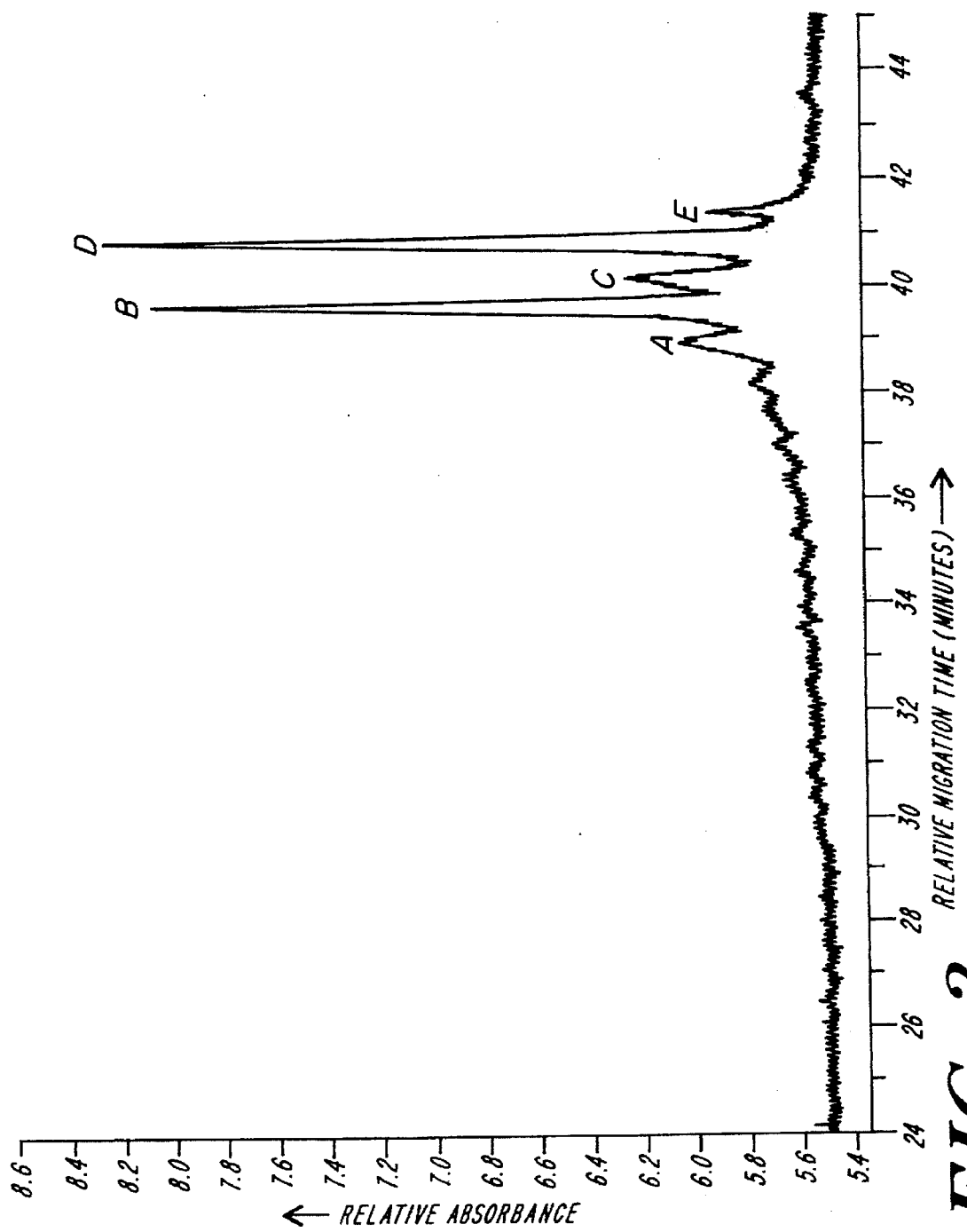
FIG. 3 is an electropherogram demonstrating the electrophoretic separation of a mixture of the 25 mer (SEQ ID NO:1), the 24 mer (SEQ ID NO:2), and failure sequences resulting from the syntheses of these phosphorothioate oligonucleotide analogs. Peak A represents the putative 23 mer failure sequence from 24 mer (SEQ ID NO:2) synthesis; peak B represents the 24 mer (SEQ ID NO:2); peak C represents the putative 24 mer failure sequence from 25 mer (SEQ ID NO:1) synthesis; peak D represents the 25 mer (SEQ ID NO:1); and peak E is unknown.

As demonstrated by the electropherograms in FIGS. 1A and 1B, this method enables the separation of oligonucleotide analogs differing in length by only one base in length. Furthermore, this method separates oligonucleotide analogs having the same length but differing only in base sequence, as shown in FIG. 3.

The used substrate, including polyacrylamide of 6% or higher T in formamide, can be easily removed from the capillary and replaced with fresh substrate, if desired. This is because the high formamide concentration in the substrate decreases its viscosity. Removal is accomplished using low pressure (about 30 to 50 psi) applied manually or with the aid of an automated system. For example, a syringe can be used to apply the pressure required to push the substrate out of the capillary.

The following examples illustrate the preferred mode of making and practicing the present invention, but are not meant to limit the scope of the invention since alternative methods may be utilized to obtain similar results.

EXAMPLES

1. HPCE Apparatus

The high performance capillary electrophoresis apparatus with UV detection and the preparation of substrate-filled capillary for the separation of DNA molecules are essentially the same as described in Cohen et al. (*Proc. Natl. Acad. Sci.* (USA) (1988) 85:9660–9663) and Heiger et al. (*J. Chromatogr.* (1990) 516:33–48). A 30 kV, 500 $\mu$A direct current high voltage power supply (Model ER/DM;

Glassman, Whitehouse Station, N.J.) was used to generate the potential across the capillary.

2. Preparation of Substrate-Filled Capillaries

Fused-silica capillary tubing (Polymicro Technologies, Phoenix, Ariz.) with inner diameter of 75 μm, outer diameter of 375 μm, effective length of 20 cm, and total length of 30 cm, was treated with (methylacryloxypropyl) trimethoxysilane (Petrarch Systems, Bristol, Pa.) and then filled with a carefully degassed 13 to 18% T polymerizing linear polyacrylamide in aqueous or formamide solution in 0.2M TBE buffer (0.2M Tris borate, 4 mM EDTA), pH 8.3, with 7 to 8.3M urea. Alternatively, capillaries were filled with a degassed solution of 13% or 18% T linear polyacrylamide. Polymerization was achieved by adding ammonium persulfate solution and TEMED. To remove impurities from the polyacrylamide, the capillary column was pre-electrolyzed at 6 kV for 30 to 60 minutes. During electrophoresis, the capillary was maintained at room temperature. Ultra-pure Trizma base, urea, acrylamide, and EDTA were purchased from Schwartz/Mann Biotech (Cleveland, Ohio). TEMED and ammonium persulfate were purchased from Bio-Rad (Richmond, Calif.).

3. Preparation of Oligonucleotides

The oligonucleotide phosphorothioate 25 mer 5'-CGTATAGCCTGATGTCATAGCCGAT-3' (SEQ ID NO:1), 24 mer 5'-GACTCGAGGTCTGCTAACCTAGAT-3' (SEQ ID NO:2), and the failure sequences from the syntheses of various oligomers having a length of up to 50 bases and up to 150 bases (base sequences unknown) were synthesized using the procedure of Beaucage et al. (U.S. Pat. No. 5,003,097), herein incorporated by reference. Briefly, oligodeoxyribonucleotides were synthesized on an automated synthesizer (Model 8700, Milligen/Biosearch, Bedford, Mass.). Both normal phosphodiester oligodeoxyribonucleotides and their phosphorothioate analogues were assembled using H-phosphonate chemistry (Andrus et al. (1988) *Tetrahedron Lett.* 29:61; Gregg et al. (1987) *Tetrahedron Lett.* 27:4051). Synthesis was carried out on a 10-μmol scale, and after the chain elongation cycles the controlled pore glass support-bound oligonucleoside. H-phosphonate was treated either with 0.2M sulfur in carbon disulfide:pyridine:triethylamine (12:12:1, volume:volume) to generate phosphorothioate internucleotide linkages. Deprotection of oligodeoxyribonucleotide was carried out with concentrated ammonia at 55° C. for 8 hours. Deprotected oligodeoxyribonucleotides were then resuspended in distilled water.

4. Separation of Oligonucleotides

Samples were electrophoretically injected into the column by dipping the cathodic end of the capillary into the sample solution and applying a voltage of 400 V/cm for 2 seconds. Separation was achieved at a typical applied field of 400 V/cm. Each column was used for multiple injections. Periodically, a short section of the capillary at the injection end was trimmed.

Figure 2:
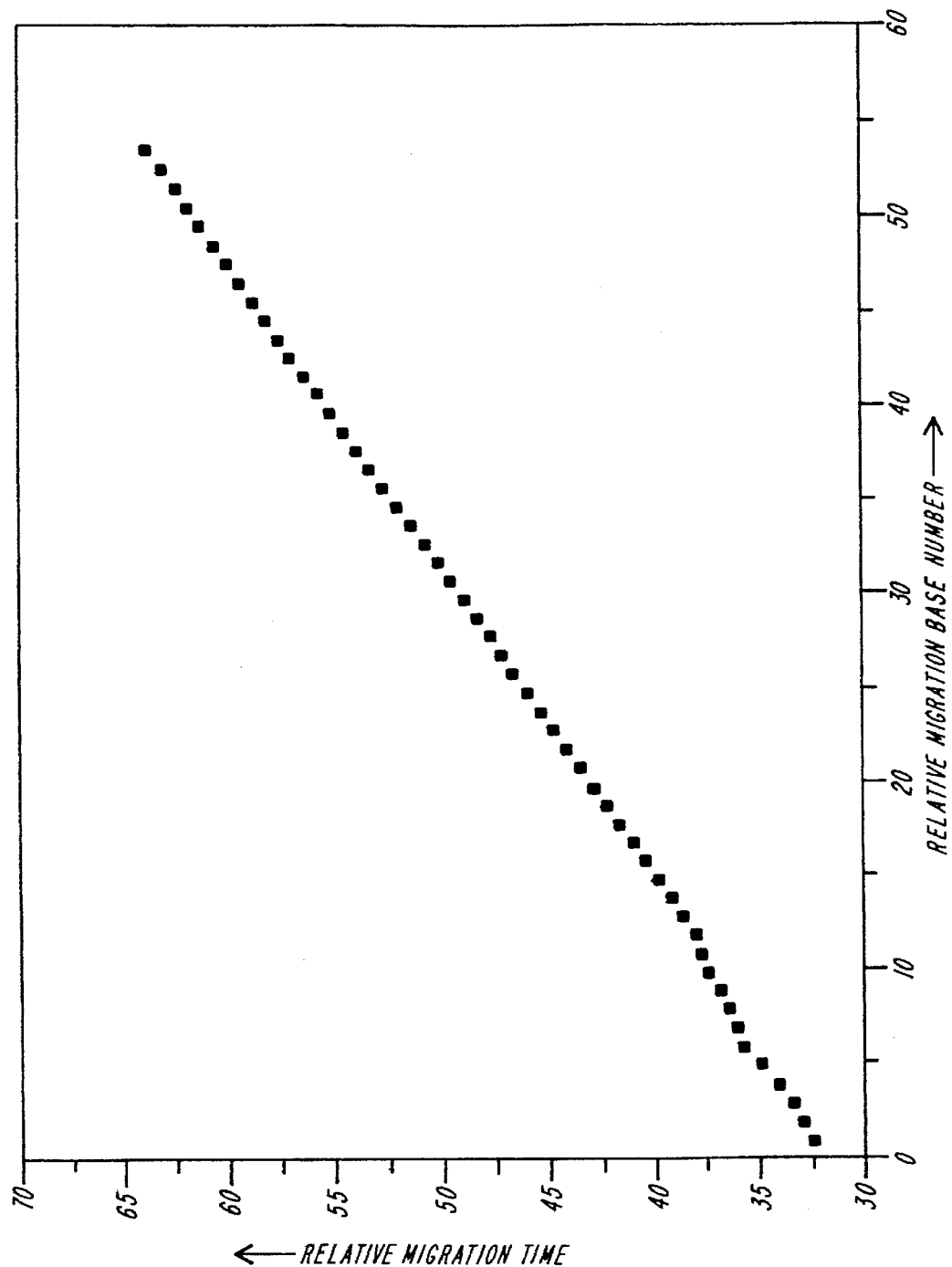
FIG. 2 is a calibration plot of migration time of the analogs separated in FIG. 1 versus base length in the analog.

The failure sequence sample (containing oligonucleotides varying in length from 1 to 50 bases, from 1 to 75 bases, and from 1 to 150 bases was suspended in water with final concentration 500 ng/ml. Each of these samples were separated on a capillary containing 15% T linear polyacrylamide. The column was developed with 60% formamide, 0.2M TBE buffer, 8.3M urea, pH 8.3. Electrophoresis was conducted under an applied electric field of 400 volts/cm and a current of 12 μA over a 20 cm migration distance. The results from the 1 to 50 and 1 to 75 base samples are shown in FIGS. 1A and 1B. When migration time was examined with respect to fragment length, a linear relationship ($r^2$= 0.9999) was observed (FIG. 2). This linear behavior of the phosphorothioate analogs is indicative of the lack of peak compression, and of migration according to molecular weight or size, each being important elements of successful oligonucleotide separation.

A sample containing a mixture of the 24 mer (SEQ ID NO:2) and the 25 mer (SEQ ID NO:1) phosphorothioate analogs (having different sequences but the same length) was suspended in water to final concentration 400 ng/ml. The sample was run on a capillary containing 13% T, 0% C, 7M urea, 0.2M TBE, pH 8.3. (The term "c" refers to a fraction: the amount of crosslinked polymer over the total monomer and cross-linked monomer). Electrophoresis was conducted under an electric field of 400 volts/cm and a current of 12 μA over a 20 cm migration distance. The results are shown in FIG. 3. The time window between elution of the 24 mer and elution of the 25 mer is large enough to accommodate an additional peak. This peak is presumed to be a failure sequence of the synthesized 25 mer and is therefore a 24 mer since this peak is migrating directly after the 25 mer under denaturing conditions. The two 24 mers are separated due to the difference in their base sequences.

5. Detection Method

Oligonucleotides were monitored by UV detection at wavelength 270 nm using a Spectra-100 spectrophotometer (Spectra Physics, San Jose, Calif.). The data were stored on an Ace IBM compatible PC computer via an analog to digital (A/D) converter (Model 970, Nelson Analytical, Cupertino, Calif.).

6. Removal and Replenishment of the Substrate

After detection of oligonucleotides in the substrate, the end of the capillary is contacted with the distal end of a series "C" Pressure Lok syringe (Rainin Instrument Co., Woburn, Mass.) with its plunger drawn out. Pressure is applied to the substrate in the capillary by gently pushing in the plunger of the syringe. Only about 30 to 50 psi pressure is required to quickly remove the used substrate from the capillary. The substrate is dispelled into a container and regenerated or disposed of. The capillary can then be refilled with fresh substrate.

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A composition comprising:
a substrate in a capillary useful for separating modified mononucleotides and oligonucleotides, the substrate comprising at lest 12% linear polymer in at least 50% (volume:volume) organic solvent, the organic solvent being a denaturing agent; and a modified mononucleotide or oligonucleotide.

2. The substrate of claim 1 wherein the substrate comprises a polymer selected from the group consisting of polyacrylamide, methylcellulose, and polyvinyl alcohol.

3. The substrate of claim 2 comprising polyacrylamide.

4. The substrate of claim 3 comprising about 12 to 20% T polyacrylamide.

5. The substrate of claim 4 comprising about 13 to 18% T polyacrylamide.

6. The substrate of claim 1 wherein the organic solvent is selected from the group consisting of formamide, urea, and sodium dodecyl sulfate.

7. The substrate of claim 6 wherein the organic solvent is formamide.

8. The substrate of claim 7 comprising about 60% formamide.

9. The substrate of claim 7 further comprising urea.

10. The substrate of claim 1 which can be removed from the capillary after use by applying from about 30 psi to 50 psi pressure.

11. The substrate of claim 1 comprising about 13 to 18% T polymerized, non-cross-linked polyacrylamide in about 60% (volume:volume) formamide.

\* \* \* \* \*